(12) United States Patent
Lenzenhuber

(10) Patent No.: US 12,651,651 B2
(45) Date of Patent: Jun. 9, 2026

(54) METHOD, APPARATUS AND SYSTEM FOR STORING USAGE DATA AND TRACKING A MEDICAL PRODUCT

(71) Applicant: Aesculap AG, Tuttlingen (DE)

(72) Inventor: Frederick Lenzenhuber, Tuttlingen (DE)

(73) Assignee: Aesculap AG, Melsungen (DE)

( * ) Notice: Subject to any disclaimer, the term of this patent is extended or adjusted under 35 U.S.C. 154(b) by 372 days.

(21) Appl. No.: 18/032,762

(22) PCT Filed: Oct. 20, 2021

(86) PCT No.: PCT/EP2021/079136
§ 371 (c)(1),
(2) Date: Apr. 19, 2023

(87) PCT Pub. No.: WO2022/084414
PCT Pub. Date: Apr. 28, 2022

(65) Prior Publication Data
US 2024/0021278 A1 Jan. 18, 2024

(30) Foreign Application Priority Data

Oct. 21, 2020 (EP) ..................................... 20202940

(51) Int. Cl.
*G16H 10/00* (2018.01)
*A61B 18/00* (2006.01)
(Continued)

(52) U.S. Cl.
CPC ............. *G16H 10/00* (2018.01); *A61B 90/90* (2016.02); *G06F 21/602* (2013.01); *A61B 2018/00988* (2013.01)

(58) Field of Classification Search
CPC .................... G16H 10/00; A61B 90/90; A61B 2018/00988; A61B 90/98; G06F 21/602;
(Continued)

(56) References Cited

U.S. PATENT DOCUMENTS 11,170,877 B2 * 11/2021 Pulitzer .................. G16H 40/20
11,250,937 B2 * 2/2022 Malvankar ............ H04L 9/3239
(Continued)

FOREIGN PATENT DOCUMENTS

CN 110197707 A 9/2019
DE 102018121682 A1 3/2020
(Continued)

OTHER PUBLICATIONS

Search Report received in European Application No. 20202940.1 dated Feb. 17, 2021, with translation, 12 pages.
(Continued)

*Primary Examiner* — Abiy Getachew
(74) *Attorney, Agent, or Firm* — Christopher A. Rothe; CM Law

(57) ABSTRACT

A computer-implemented tracking method, an apparatus, a tracking system for storing usage data of a medical product, and a computer-readable storage medium. The method includes the steps of detecting usage of the medical product, creating the usage data which relate to the detected usage of the medical product, and storing the usage data in a data record in a form which cannot be modified retrospectively, specifically in a blockchain.

18 Claims, 6 Drawing Sheets

(51) Int. Cl.
    *A61B 90/90*         (2016.01)
    *G06F 21/60*         (2013.01)

(58) Field of Classification Search
    CPC .. G06F 21/64; H04L 67/1095; G06Q 10/0639
    See application file for complete search history.

(56) References Cited

U.S. PATENT DOCUMENTS

| | | | |
|---|---|---|---|
| 2007/0135965 A1* | 6/2007 | Nguyen | A61G 12/001 |
| | | | 700/231 |
| 2018/0096121 A1 | 4/2018 | Goeringer et al. | |
| 2018/0198604 A1 | 7/2018 | Hayton et al. | |
| 2018/0211718 A1* | 7/2018 | Heath | G16H 80/00 |
| 2019/0065681 A1 | 2/2019 | Gmeiner | |
| 2019/0206569 A1 | 7/2019 | Shelton, IV et al. | |
| 2020/0042925 A1 | 2/2020 | Ramani et al. | |
| 2020/0143085 A1 | 5/2020 | Cooner | |
| 2021/0315655 A1 | 10/2021 | Lenzenhuber et al. | |
| 2021/0343401 A1* | 11/2021 | Joseph | G16H 40/20 |
| 2021/0378779 A1 | 12/2021 | Lenzenhuber et al. | |
| 2022/0008155 A1 | 1/2022 | Hoegerle et al. | |

FOREIGN PATENT DOCUMENTS

| | | | |
|---|---|---|---|
| DE | 102018125884 A1 | 4/2020 | |
| DE | 102018126969 A1 | 4/2020 | |
| DE | 102018133503 A1 | 6/2020 | |
| JP | 2006018564 A | 1/2006 | |
| JP | 2018109994 A | 7/2018 | |
| JP | 2018121328 A | 8/2018 | |
| JP | 2020010267 A | 1/2020 | |
| WO | 2019238972 A1 | 12/2019 | |

OTHER PUBLICATIONS

Search Report received in International Application No. PCT/EP2021/079136 dated Jan. 20, 2022, with translation, 6 pages.
Written Opinion received in International Application No. PCT/EP2021/079136 dated Jan. 20, 2022, with translation, 17 pages.
Office Action received in European Application No. 21 794 864.5-1218 dated Jul. 23, 2025, with translation, 19 pages.
Office Action received in Japanese Application No. 2023-524455 dated Jun. 6, 2025, with translation, 36 pages.
Notice of Allowance received in Japanese Application No. 2023-524455 dated Dec. 12, 2025, with translation, 2 pages.

* cited by examiner

METHOD, APPARATUS AND SYSTEM FOR STORING USAGE DATA AND TRACKING A MEDICAL PRODUCT

CROSS-REFERENCE TO RELATED APPLICATIONS

This application is the United States national stage entry of International Application No. PCT/EP2021/079136, filed Oct. 20, 2021, and claims priority to European Application No. 20202940.1, filed Oct. 21, 2020. The contents of International Application No. PCT/EP2021/079136 and European Application No. 20202940.1 are incorporated by reference herein in their entireties.

FIELD

The present invention relates in general to the use of medical products. In particular, it describes the storage of data about the use thereof in a manner that is tamper-proof, at least to the extent that is generally technically feasible and economically reasonable at present. In particular, the present disclosure relates to a tracking system for secure and reliable tracking of at least one disposable medical product and to a tracking method.

BACKGROUND

The following description of the prior art serves to provide a better understanding of the invention and in particular the advantages of the invention.

Currently, it is difficult to ensure limited re-utilization of medical products, in particular only one-time use for hygiene or contamination reasons, or only a certain number of re-utilizations for reasons of wear and tear or shelf life. Accidental application beyond the permitted use may occur inadvertently if proper labeling, instructions for use, or designation and other precautions that may have been taken for the products are not followed.

Furthermore, with the prior art available, unintentional or intentional application beyond the permitted use cannot be ruled out, nor can it be traced in retrospect. The determination of such an unintentional or intentional application beyond the permitted use can only take place on the basis of circumstantial evidence such as wear and tear appearance/wear out and customer statements.

Currently available and used database solutions such as SQL, MYSQL, SAP, Oracle, etc. do not adequately meet the requirement of tamper-proof content. The data in such databases can be changed at will at any time in some circumstances, even if the need for administrative rights to make such changes provides a certain level of security, it is still not clear from the data whether the stored data is correct.

In addition, the solutions of the prior art are to some extent vulnerable to attacks by third parties and thus potentially falsifiable.

SUMMARY

The object of the invention is to overcome or at least reduce the disadvantages of the prior art described above, to improve the prior art, and/or to provide at least one useful alternative to the existing prior art. In particular, an object of the present invention is to provide a (tracking) method, a (tracking) device, and a (tracking) system for tracking a medical product, which tracks a medical product to be tracked, in particular a disposable medical product, in a secure and tamper-proof manner, in order to ensure or at least support a limited number of uses of this medical product, to be able to make a reliable statement about an (application) state of a medical product and to increase a safety of a patient. In particular, the aim is to document the historical course of a medical product with data in a tamper-proof manner. Another partial object can be seen in ensuring that a medical product is tamper-proof.

In particular, the present invention solves the object by detecting a use/application of the product, creating usage data/use data/application data relating to the detected use of the product, and storing the use data in a dataset in a retroactively non-modifiable form. A 'retroactively non-modifiable form' is in particular also to be understood as a form of storage that is not changeable from an economic point of view, for example because an effort for change is uneconomically large. For storing the use data in the dataset, blockchain technology is used according to the invention, which prevents the retroactive modification of the data quite well. By storing the dataset as a blockchain dataset, decentralized storage can be realized, whereby storage can be realized that is secured against the failure of individual servers. Especially in the area of medical products, high reliability is an advantage. In addition, it has to be ensured that the storage of the dataset and an evaluation of already stored datasets can also be realized decentrally without a permanent connection to a server. This can be achieved by using blockchain technology for the dataset without increasing the risk of retroactive modifications at the same time.

In particular, the object is solved by providing a medical tracking system for secure tracking of at least one disposable medical product, comprising: a disposable medical product to be tracked, which has a bijective/one-to-one identification (i.e. assigned only once), in particular a bijective serial number and/or an ID element; at least one detection unit, in particular a reading device, adapted to detect the identification of the disposable medical product and to provide it in a computer-readable form; a computer network with at least three computers/data processing units/nodes, on each of which a digital tracking book with a directory of information blocks relating to the at least one disposable medical product is stored in a decentralized manner as/in the form of a blockchain, wherein in particular at least the unique identification (or data of the identification) of the at least one disposable medical product and a first (cryptological) hash (in particular as checksum) are stored in a first (genesis) block; an application module adapted to send an application transaction for the disposable medical product to the computer network upon detection of the disposable medical product by the detection unit/detection device (before or during an application); a block generation module adapted to create (on the basis of the application transaction) an application block with (the first hash), a time stamp, the application transaction, and an application hash and to make it available to the computer network in order to add this application block to the respective blockchain in the computers of the computer network; and a tracking (alarm) module adapted to read out the blockchain for the at least one disposable medical product and to detect an existing application block in the blockchain and to issue an alarm and/or lock an application of the disposable medical product if an application is detected again (i.e. presence of an application block with application transaction for the medical product). In this way, it can be ensured (in particular on the part of the manufacturer) or at least supported that the disposable medical product is only used once and, for example, that a requirement for a sterile standard is met. In particular, the issuing of the alarm is appended as an alarm transaction in the blockchain to ensure secure documentation about a warning of the user and to have clear proof.

According to an embodiment, the identification, in particular the serial number and/or a QR code, may be engraved in the disposable medical product, in particular may have a laser marking (may be lasered in), and the detection unit may have an optical detection unit, in particular a camera, and/or the identification, in particular the serial number, may be stored in an RFID tag of the disposable medical product and the detection unit may have an RFID reader/RFID reading device. In this way, the identification is inseparably linked to and stored on the disposable medical product and can be read by a compatible reader/reading device. In the case of the engraved serial number and an RFID tag, preferably sealed from the environment, a requirement for sterility of the medical product can be ensured and in particular can be read by a contactless reading device. Security is further increased.

According to a further embodiment, the at least one disposable medical product may be a medical, in particular surgical, instrument and/or a sieve basket and/or a holder and/or an electrically operated medical device. Seamless and secure tracking is particularly important in these cases and can be efficiently realized by the tracking system. A surgical (disposable) instrument, for example, is to be used during an operation and is not to be used again afterwards. For this purpose, the instrument is detected by the detection unit before an application and the application transaction is added to the blockchain accordingly. In the event of a repeated (unauthorized) application of the instrument by detection via the detection unit, the blockchain reads the application transaction and determines that the instrument is no longer usable. In a further preferred embodiment, it may be provided that a sterilization transaction is written to the blockchain when the medical product has been sterilized, and the tracking module reads the blockchain and determines that no application is present in an application transaction with a sterilization transaction following the application transaction and that a repeated application is permitted without issuing an alarm and/or blocking an application. In this way, sterility of the medical product is always ensured.

Preferably, the disposable medical product may be an electrically operated medical device and the tracking module may be adapted to interrupt an electrical power supply to the disposable medical product upon a repeated application or, respectively, during reading of an application transaction to this medical product. In this way, unintentional use of a non-sterile disposable product is reliably prevented.

Furthermore, the tracking system may preferably comprise a display device on which an alarm is visually output as soon as a repeated application of the medical product has been detected. In particular, a user has to make an input, in particular on a touch display of the tracking system, in order to be able to continue using the medical product, in particular an electrically operated medical device, contrary to the warning, for example, if the medical product is to be used a further time due to an emergency. A corresponding transaction can be detected in the blockchain of the computer network. In this way, it is also documented if a disposable medical product is used more than once contrary to a specification. In addition to the visual alarm, an acoustic alarm may also be issued via a loudspeaker.

According to an embodiment, the tracking system has a central database on at least one computer, in which additional entries/data on the at least one disposable medical product are stored. In particular, data such as operating instructions or sterilization instructions for the medical product are stored in the database, wherein a unique hash value (entry hash) has been generated for the entries/data, in particular the operating instructions, which is stored in the blockchain for the medical product in order to ensure that the data stored in the database is tamper-proof. Since only limited amounts of data can be stored in the blockchain, a file (data) such as instructions, a picture of the medical product or documentation is stored in a standard database, for example, and a hash procedure is used to generate an (entry) hash as a kind of certificate seal for this file (as data), and this unique (entry) hash is stored in the blockchain for the medical product. If, for example, an instruction in the central database is changed (even just a single bit), the entire hash changes and no longer matches the tamper-proof hash of the blockchain. In this way, manipulation can be prevented by appropriate verification. In this way, important data with a large file size can be stored centrally and can be secured against falsification via the entry (hashes) of or respectively in the blockchain. A hash value is a short string of characters that requires only a few bytes of storage space and can therefore be efficiently further maintained in the blockchain.

Preferably, in addition to the bijective identification of the at least one disposable medical product, a minimum durability date (MDD) may also be stored in the first (genesis) block, and the tracking module may be adapted to compare the minimum durability date with the current date when it is detected by the detection unit and to issue an alarm and/or lock an application of the medical product if the MDD is exceeded. In addition, an article number may be stored in the (genesis) block for assignment of the medical product.

In particular, the application module may be adapted to add a dead-end marker to the corresponding medical product of the blockchain in addition to the application transaction in order to reliably and quickly recognize that the corresponding medical product is no longer usable in the event of a repeated application. In particular, the application module may add a dead-end marker to the blockchain if the minimum durability date is exceeded.

According to a further embodiment, a warehouse-entry detection device may detect the unique identification of the medical product and add a warehouse transaction with a warehouse entry date (as a time stamp) to the blockchain for the medical product to document a warehouse entry. In particular, the warehouse-entry detection device is adapted to determine, via a data connection to a warehouse data hotspot, that it is the location of a warehouse (and not, for example, a location of the application).

According to a further embodiment, a sale-detection device may detect the unique identification of the medical product and the tracking system may add a sale transaction with a sale date (as a time stamp) and further preferably a customer number in the blockchain for the medical product to document a sale of the medical product.

According to a further embodiment, a shipping detection device may detect the unique identification of the medical product and add a shipping transaction with a shipping date (as a time stamp) to the blockchain for the medical product in order to document a shipment of the medical product. With these detection devices and the respective transactions stored in the blockchain, it is possible to securely and bijectively document and track the complete path of the medical product from manufacture to application.

In particular, the tracking system may be adapted to determine a location of the detection device in order to execute a transaction corresponding to the location via the location. For example, if a medical product is scanned by the reading device in the warehouse, the reading device determines its location in the warehouse (e.g. via a localization system (GPS) or a data connection (WLAN hotspot warehouse)) and subsequently carries out a warehouse entry transaction. In this way, a standardized detection device can be used to detect the individual stations of the medical product and can assign the detection device as a warehouse-entry detection device.

In particular, the tracking system may have a sidechain for a temporary interruption of the connection to the computer network with the (main) blockchain, in which an application transaction is temporarily written and, when a connection is established to the computer network with the (main) blockchain, the deposited transactions are written (with a time delay) to the blockchain.

Furthermore, the object with respect to a (tracking) method is solved in particular by providing a computer-implemented medical tracking method for secure tracking of at least one disposable medical product, in particular for a medical tracking system according to the present disclosure, comprising the steps of: detecting a bijective identification of a disposable medical product by a detection device; calculating, based on the bijective identification, a first hash value; storing a first (genesis) block with the detected identification in a blockchain on each computer of a computer network comprising at least three computers; detecting an application/use of the disposable medical product by a detection device and sending an application transaction to the computer network; checking whether an application block exists in the blockchain for the disposable medical product; if no application block exists yet: generating, based on the application transaction, an application block with the first hash, a time stamp, the application transaction, and an application hash, and providing it to the computer network to add this application block to the blockchain in the computers of the computer network, respectively; and if an application block exists: issuing an alarm and/or blocking a functionality of the disposable medical product.

According to a preferred embodiment, an NFT (non-fungible token) may be stored as a digital twin in the blockchain. As soon as, for example, an article number and a serial number of the medical product are known, the digital twin can be created and tracked. In a first step, a digital twin is stored in the blockchain, in particular with at least the article number, the serial number and a UID. In particular, a time stamp of sterilization may be deposited at a step of sterilization. In particular, at least one or a combination of the following time stamps may be stored with corresponding transaction:

start of production,—end of production,—quality inspection,—supply to the warehouse,—sale, in particular with customer ID,—packaging,—shipping, and/or—arrival.

According to a further preferred embodiment, at least one or a combination of the following time stamps may further be stored with corresponding transaction:

feeding CSSD,—manual pre-cleaning,—cleaning in the washer-disinfector,—maintenance,—packing the sieve,—packaging in the sterile container and/or sterile sieve (basket),—sterilization,—provision in OR.

According to an embodiment, the tracking system may detect the application of the disposable medical product by reading the unique identification by the detection unit and by a stored association of the detection device as an application-detection device with the application.

According to a further embodiment, the tracking method may further comprise the steps of: in addition to the bijective identification with a bijective serial number: storing a unique control number associated with the serial number in the first block generated by a predetermined non-public algorithm as an alphanumeric numeric code, upon detection of the application of the disposable medical product: verifying the serial number and the control number associated with the serial number and determining that the disposable medical product is counterfeit if the control number does not match the serial number. The serial number is encrypted using a private and publicly unknown algorithm and an associated control number is created, which is also stored in the blockchain. A corresponding checking algorithm can be used to check whether the control number actually matches the serial number. This prevents falsification with a continuous serial number, since an 'encrypted' and changing control number is required in addition to the continuous serial number.

The use data may also be transmitted from the product being used to one or more computers and stored there. In this context, computer means any type of data processing device.

In this case, the blockchain dataset on the one or more computers may be integrated in an existing data construct that may also be based on blockchain.

The storage on the product or the computers may be configured differently. It is possible that the storage locations are all non-public, e.g. within a company or a hospital. The computers, however, may also be distributed, non-publicly located, e.g. at the manufacturer, service partner and user of the product. Or, the storage is performed in a publicly accessible DLT.

The data transmission used in this process may be accomplished by various technologies, for example: Bluetooth, IR, LAN, WLAN, IoT, mobile radio, e.g. 2G, 3G, 4G, 5G, GSM and/or LTE, LoRaWAN (Low Range Wide Area Network). However, other wired or wireless protocols or transmission technologies may also be used. In addition, direct transmission or transmission via intermediate stations, such as smart hubs, repeaters, routers, switches, mobile hotspots, data gates, access points, and/or the internet is possible.

Additional information may also be stored in the stored datasets or data constructs. In particular, information on the article and/or serial number of the product and/or a permitted use, such as an expiration date after which the product may no longer be used, or a permitted number of uses is stored in the datasets. This information may either be written to the data construct when the product is manufactured, or it may be detected when the use is detected and then stored in the dataset. Other information that may be stored is, for example, information regarding dates of manufacture, warehousing, shipment, sale of the product.

The additionally stored data may be used to determine, when a use is requested from the product, whether this requested use is permitted or represents an unauthorized use. This is done by evaluating the data stored in the dataset and/or the data construct. For medical products, storage in the form of a blockchain thus represents a particularly advantageous configuration.

If it is determined that the further use is an unauthorized use, the unauthorized use can be recorded in a tamper-proof manner. Alternatively or additionally, a signal may be issued, e.g., acoustically and/or optically. Furthermore, additionally or alternatively, data may be transmitted that triggers such a signal at another device or causes a notification there. Furthermore, alternatively or additionally a request may be issued and the product may be released for use only after confirmation of the request, e.g. by a user. This enables emergency use, for example, so that a product that is actually no longer to be used can still be used. Reasons for this may be, for example, that no unused product or product to be used within the use parameters is available. Finally, as an alternative to this or in addition, the product may be locked for the requested further use, so that it cannot be employed for the use determined to be an unauthorized use. This may increase overall safety, since a product may pose a safety risk after reaching the allowed use times or number of uses, e.g., in the case of cutting tools, the cutting edges may potentially cause damage.

Further advantages of the invention are the tamper-proof documentation of the use of products. This makes it possible to detect unauthorized use and, by preventing such use, to increase general safety during utilization.

Any disclosure relating to the (tracking) method of the present disclosure also applies to the (tracking) system according to the present disclosure as well as vice versa.

BRIEF DESCRIPTION OF THE DRAWINGS

The preceding summary, as well as further objects, features and advantages of the present invention, are further explained by and with reference to the following figures, so as to provide a better understanding of the invention. Herein, identical reference signs denote identical elements.

The following is shown.

DETAILED DESCRIPTION

Figure 1:
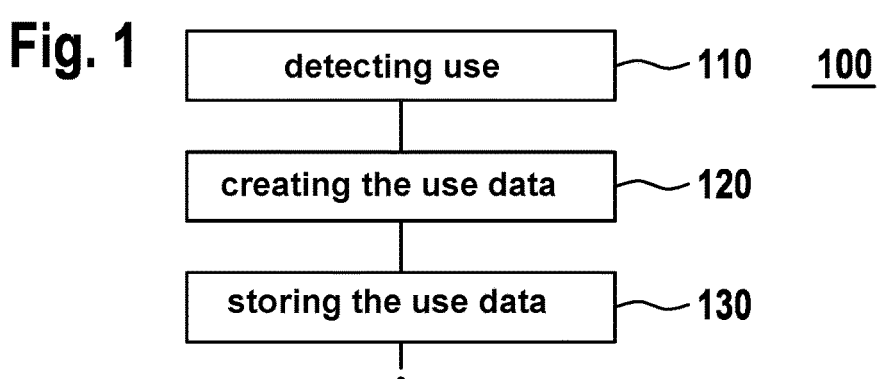
FIGS. 1 to 4 show flow diagrams of a method according to preferred embodiments.

In order to ensure this limitation for products that are only to be used a certain number of times or only during a certain period of time, or the like, proof of the uses is required. Ideally, such proof should be tamper-proof so that it is not possible to add, delete or change uses at a later date. In order to fulfill the aspect of verified proof and to be able to release reliable information as a manufacturer as well as a customer of a product (e.g. quality management of a hospital, material management of companies, or the like), and thus to increase legal certainty in the case of critical applications, a solution is proposed which ensures that the data is tamper-proof in the form of logs and thus documents the uses in a historically secure manner. The manufacturer of the products, the user(s) of the products, i.e. those who directly carry out the use, but also possibly all parties in the supply chain between manufacturer and user are usually interested in the use of products. These may be distributors, but also possibly intermediate stations such as material storage points and central administration points, e.g. in a hospital network. Manufacturers and users are also covered by the term 'parties' in the following.

The preferred method for this is what is known as distributed ledger technology (DLT for short), which is explained briefly below. DLT is used for the documentation of certain transactions. In contrast to the classic approach, in which a general ledger is usually managed by just one instance, here any number of copies of the ledger, which are in principle identical, are maintained decentrally by different parties. Appropriate measures are taken to ensure that new transactions are added to all copies of the ledger and that there is agreement (consensus) on the current status of the ledger.

DLT is one form of blockchain, others are, for example, tangle. In the following, the umbrella term blockchain is used, but the invention may also be implemented with any other blockchain technology.

This solution has, inter alia, the following exemplary advantages. A user (e.g. manufacturer, operator or distributor, etc.) can use the blockchain to validly determine and log whether a product has been used more than the specified maximum number of times. For example, it can be determined whether a single-use item (a product that may only be used once for hygienic reasons, for example) has been used multiple times. The user can also ensure that products are only used once. This can be done by locking (e.g., for current-carrying devices) or by signal notices (e.g., acoustic, optical signals) or even a request in a dialog of a computer. Such notices or signals can be sent, for example, to computers, mobile devices, software operated on such devices (e.g., programs on computers, apps on mobile devices), displays on control devices for the products, or other information channels. Various transport protocols can be used for this purpose. For example: SMS, email, TCP/IP etc., or data transmission via Bluetooth, IR, LAN, WLAN, IoT, mobile radio, e.g. 2G, 3G, 4G, 5G, GSM and/or LTE, LoRaWAN. Likewise, communication can take place either directly or via intermediate stations, such as smart hubs, repeaters, routers, switches, mobile hotspots, data gates, access points, and/or the internet.

By securely logging the uses, all parties involved can ensure or respectively even increase their quality and avoid accidental multiple use or too frequent use of products and present valid data and evidence to monitoring institutions or authorities.

Tamper-proof logging is a technology for the future and any party using such logging will be prepared for future requirements. Every party involved can establish itself as a party in a blockchain and thus enhance its reputation vis-à-vis institutions and authorities. This may be decisive for the economic assignment of contracts. Falsification of data can no longer occur through the implementation, as the history is mapped via the respective blocks. In addition, application cycles can also be logged validly and unalterably for reusable products.

Previous solutions involve logging or recording use data in conventional databases such as mySQL, SQL, etc. Some of these are cloud-based. Such solutions are usually not tamper-proof. It is also possible that data is entered into such databases by users themselves and is therefore also subject to errors in data detection and/or data input. In addition, data in such databases can be changed by IT administrators (with so-called administration rights, i.e., extended access to the data) or by unintentional access (e.g., attacks) by third parties. Such changes may only be noticed relatively late, so that countermeasures can only be initiated with a time delay. Overall, this leads to a high level of administration and monitoring effort. There are also no limits to fraudulent intentions regarding database changes and data manipulation with sufficient criminal energy.

In order to strengthen the integrity of parties towards institutions and authorities, the use of blockchain is a beneficial approach.

Products with limited use, in particular single-use products, are provided to customers for their intended, e.g. one-time, use and are usually marked or described accordingly. Single-use products may, for example, be marked accordingly by a symbol of a crossed-out number 2.

This symbol can be found, for example, on product packaging, labels, on the products themselves, instructions for use and other appropriate places that may be prescribed.

As an example, the solution is illustrated below using a tool, but is not limited to this alone. Rather, the explanation extends to any single-use products or products with limited use.

In general, the invention requires that products can be detected and recognized electronically. This is described in the prior art, e.g. in DE 102018133503 A1, DE 102018126969 A1, DE 102018121682 A1.

Also known from the prior art are so-called smart hubs, mobile hotspots, data gates, access points, repeaters, etc., which provide a connection between devices and/or to the internet.

This ensures basic availability and reachability of services on the internet and/or at other parties. Examples of such devices include mobile hotspot over the mobile network (5G, 4G, 3G, dual band, etc.), base devices for IoT devices, smartphones or WLAN routers that can establish a hotspot, LoRaWAN that use a technology that is being established as one of the possible foundations for TOT devices alongside 5G, and the like.

Furthermore, the functionality is described to be able to communicate with at least one blockchain and to execute transactions or respectively to insert information (into blocks).

In general, the complete life cycle of a product, if applicable with sub-process steps, may be recorded, i.e. logged, in the blockchain.

Figure 9:
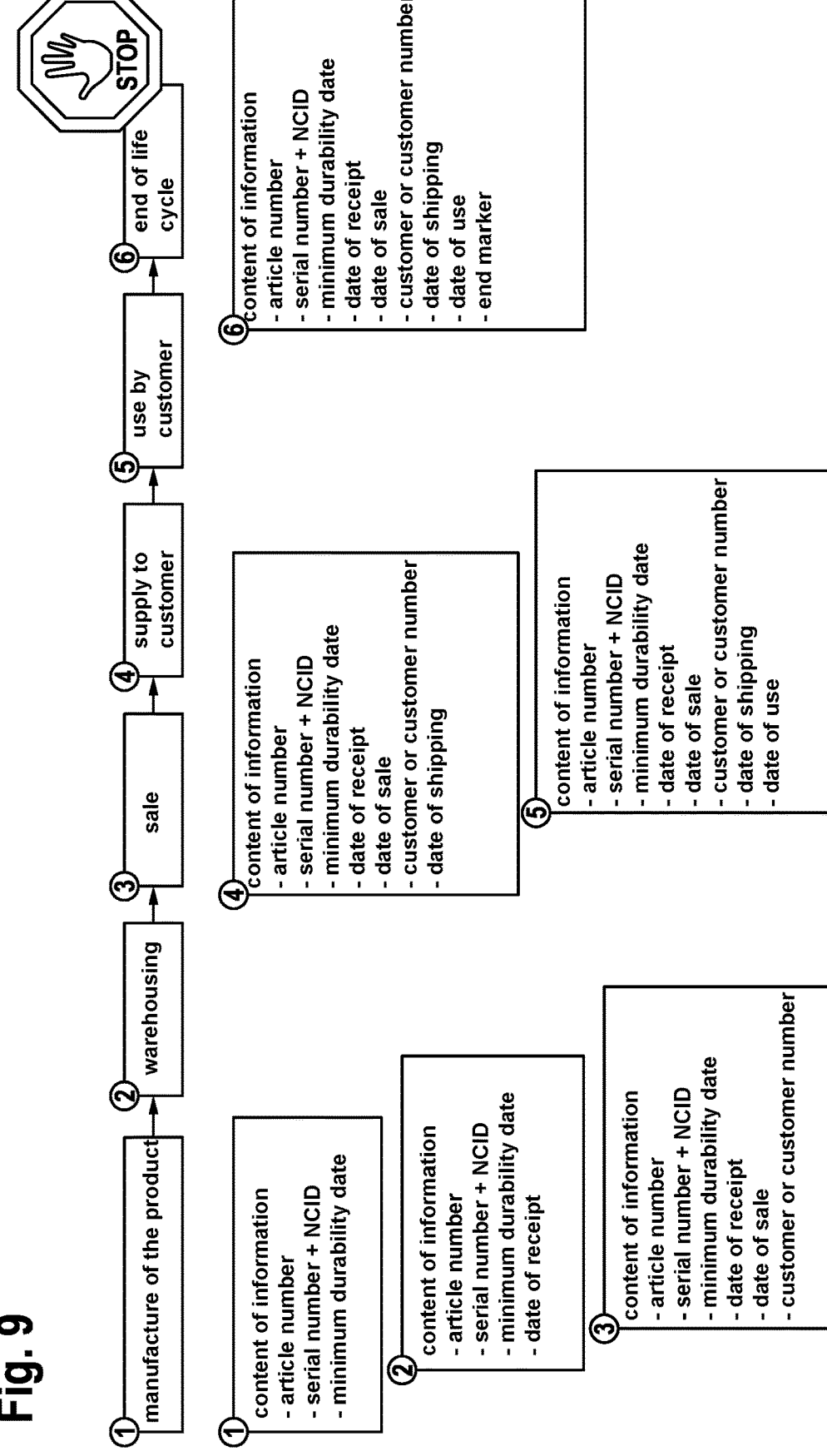
FIG. 9 shows a flow diagram of a method according to a preferred embodiment with additional data.

Some possible phases of the life cycle are described below by way of example. These are shown in FIG. 9. For each phase, the content of the stored data is shown as an example. The data shown in FIG. 9 is for illustrative purposes only; further data may be stored, as explained in this description, and data may also be omitted, depending on the particular application.

Phase 1 is the manufacturing of the product. During the manufacturing process, the product is manufactured and finally loaded with data. This is done in the form of laser marking or writing data memories, or the like. Such processes are described, for example, in DE 102018125884. According to the present description, this may involve, for example, an article number, e.g.: GP111SU, a unique serial number, e.g. SN0001020, possibly including a uniquely assigned data sequence, e.g. a NONE COPY IDENTIFICATION, abbreviated NCID, which may optionally also be encrypted, and/or a minimum durability date, e.g.: 2019-09 for September 2019, may be logged. One or more of these pieces of information may also indicate, for example, that the product is provided for single use only, i.e. Single Use. This may be indicated, for example, by the letter combination SU in the article number or serial number. Optionally, data may also be stored separately indicating the property single use, reusable, the number of permitted uses or the period of a permitted use. In this way, counting of use cycles is also possible.

Phase 2 describes the warehousing of the product. Here, data is added to the already logged dataset, indicating, for example, the day of warehouse entry and thus the saleability. This data is written to the blockchain in addition to the already existing data packet. Further information describing the entry to the warehouse, and the previously traveled routes and intermediate stations of the product are also possible, e.g. day of shipment from the factory, indication of the transport phase, quantity and number of intermediate stations, transport duration, traveled distance of the product, etc.

Phase 3 describes the sale of the product. Here, data is added to the already logged dataset e.g. showing the time of placing the product on the market. This may be done as a day only or with additional information such as time, location, time zone, etc. This data is written to the blockchain in addition to the existing data packet. Additional information is also possible, e.g. price, quantity and number of owners, identification of the owner, identification of the buyer, identification of the seller, etc. The previously described identifications may also be made in the case of desired anonymity via encrypted ID data, e.g. numbers, symbols, and the like, which are only known to a limited extent, e.g. only to the manufacturer, or only to public authorities.

Phase 4 describes the shipping of the product. Here, data is added to the already logged dataset, e.g. showing the time of the shipment. This may be done as a day only or with additional information such as time, location, time zone, etc. This data is written to the blockchain in addition to the existing data packet. Additional information is also possible, e.g. day of previous shipment, indication of transport phase, quantity and number of intermediate stations, transport duration, distance travelled by the product, identification of the sender, identification of the recipient, transport restrictions such as fragile or no air freight in order to avoid increased air pressure, etc. The previously described identifications may also be made in the case of desired anonymity via encrypted ID data, e.g. numbers, symbols, and the like, which are only known to a limited extent, e.g. only to the manufacturer, or only to public authorities.

Phase 5 describes the actual use of the product. Here, data is added to the already logged dataset, e.g. showing the time of use. This may be done as a day only or with additional information such as time, location, time zone, etc. This data is written to the blockchain in addition to the existing data packet. Additional information is also possible, e.g. writing out cached use data in the device since the last connection to the detection unit, identification of the person or device using the product, which can be detected e.g. via identification before use, further data of the use, i.e. type of use, duration of use, quantity and number of uses, number of switch-on and switch-off operations, or actions performed during use. The previously described identifications may also be made in the case of desired anonymity via encrypted ID data, e.g. numbers, symbols, and the like, which are only known to a limited extent, e.g. only to the manufacturer, the owner, or only to public authorities.

Phase 6 describes the end of the life cycle. It is determined, e.g. by the product itself or another device, on the basis of the previously stored data, e.g. quantity and/or number of uses already stored, daily data of the stored uses, etc., that the end of the life cycle of the product has been reached.

The product is thus marked as out of date, or expired, for example, and it is therefore considered that this product should be disposed of and not used again. The time at which the product was marked as 'expired' may also be recorded.

If corresponding data is stored in the blockchain for the product, the use may also be stored in phase 5 specially marked, e.g. as off label use, and/or the product may be locked for use if the technical possibilities are available. If, for example, a product that is marked as 'expired' would be detected again in a use environment on a later day or after a defined period of time, an off label use can be determined as mentioned above. This reduces both patient and operator risk.

The locking of the product, or respectively the interposition of a safety query before use, can now be prescribed for the product. For devices with power supply, for example, switching on can be technically prevented.

In order to enable emergency operation nevertheless, a user may confirm the interposed prompt, which in turn can be stored in the blockchain in phase 5 via additional data in the dataset. This may again be done with the identification of the user or the using device described above. Otherwise, a product that has not yet reached the end of its lifecycle would have to be deployed.

There are several alternative options for this case:

The user is not informed. The off-label use is only logged. The relevant party, e.g. the company or institution where the product is used, can view the product data in the blockchain and determine if a product has been used more than once. If applicable, a quality assurance officer may then intervene and have the product removed from the cycle.

During use, or respectively at the start of use of the specific product, the user receives information indicating the end of the life cycle. This may be done via an acoustic or visual display on the product or on a suitable device involved in the use. Such suitable output devices may include, for example: tablet, control device, smart watch, display, screen in the use space, and any suitable output device. Where appropriate, the indication of permitted use may be provided along with an indication of whether the product is even suitable for the intended use.

The output of a corresponding notice may also be carried out at another location. Either at an output device at a central monitoring point or also as feedback to the manufacturer. From there, a service technician or sales person can then be sent to the customer to advise on the use.

For the further course in the life cycle, such as return, maintenance, reprocessing, recycling and/or disposal, the same or similar data as described above may be stored in the blockchain.

For all exemplary phases described above, the product is generally detected by an electronic reader for storing the data. This may be done, for example, by reading a barcode, in 2D or 3D, or an NFC (Near Field Communication) tag on the product, outer packaging or shipping packaging. Assignment via the shipping packaging is also possible using an intermediate database query.

This method of using DLT/blockchain technology provides legal certainty and improves integrity vis-à-vis institutions and authorities. Likewise, the reputation of all parties using this solution increases. This leads to improved standing with distributors, contractors and end customers.

The DLT or respectively blockchain can be used in different variations. One possibility is a so-called private blockchain. Here, the blockchain is operated within a closed network within a company or institution and is possibly kept redundant on several servers. These servers are regarded as so-called nodes/masternodes. The block contents are therefore not visible to other parties outside the private network. Nevertheless, a corresponding data transmission can take place in order to be able to provide a corresponding proof.

Another possibility is a semi-private blockchain. Here, for example, the blockchain may be managed and jointly operated, i.e., written to, by two or more parties involved. Alternatively, read-only access for some parties is also possible. An example here is the operation of the shared blockchain by user and manufacturer, so that, for example, a re-order of expired products can be automated. The block contents are thus not visible to other parties outside the semi-private network. Nevertheless, a corresponding data transmission can take place in order to be able to carry out a corresponding proof.

Another possibility is a public blockchain. Here, the blockchain is operated publicly and all parties, possibly even uninvolved parties, i.e. the public, can view the transactions, i.e. the block contents. The data which is written in it may be stored in plain text or in encrypted form, which in turn can create a certain degree of anonymity. For this purpose e.g.: masternodes may be operated at various company locations around the world. If applicable, customers with their own masternodes are integrated into the network. Furthermore, an adaptation to an already existing blockchain such as Ethereum, NEO, or Cardano is conceivable in order to feed the data to be written there.

In addition, there is the possibility of also detecting and storing the use of products if there is temporarily or permanently no connection to the blockchain used, e.g. via the internet in the event of a failure of the latter. This can be done, for example, with a so-called sidechain. In this case, a so-called sidechain can be established on the product or a device that is in communicative connection with the product, parallel to the blockchain actually used. This may also be done ad hoc, i.e. without preparation, when a data communication error is detected. In this way, an independent, continuous blockchain can be operated locally, which first generates blocks locally and records, i.e. logs, product use locally.

If, in the case of an only temporarily interrupted connection, the connection is restored, or in the case of a permanently missing connection, the connection can be specifically established, e.g. as part of maintenance, preventive maintenance, a service technician deployment, or another planned data transmission, a connection can be established to the actual blockchain, in this case the main blockchain, and the data content of the sidechain can be transmitted to the main blockchain or can be integrated into it. The data blocks of the sidechain are then stored as additional blocks in the main blockchain, for example. This variant also makes it possible to integrate products that are operated without a data connection, i.e. offline, into the blockchain, albeit with a time delay. Medical products can thus be used with high availability without having to sacrifice the advantages mentioned. Hardware requirements can be kept low, since only a sidechain is generated and stored locally. Complex mechanisms for replication and synchronization of classic databases can be dispensed with, which means that high availability can be achieved.

Another advantage of the solution is the increased security with regard to counterfeit products. Data such as the serial number is stored for a product in the blockchain with a unique control number, which is generated via an algorithm and consists, for example, of a unique alphanumeric code. If a counterfeit product with the same serial number and an attempted falsified control number is subsequently detected, this product is declared as a counterfeit and the user, or customer, or the currently acting party is informed and/or this is logged in the blockchain. Patient safety can be increased. Counterfeit products may also be detected by other methods, such as checksum comparison or comparison of an attached encrypted dataset (e.g. a control number) with a primary key stored on a server (e.g. in the cloud, i.e. on remote storage accessible via data communication). This can be used to determine whether the product is authentic or a counterfeit. The encryption used itself can then be decoded with the primary key and can be compared with the dataset previously stored (e.g. with the manufacturer or another party in the supply chain). In this way, the authenticity can be verified and the potentially dangerous use of counterfeit products can be avoided.

An operation of databases does not exclude the application of blockchain technology. Both technologies can be used together. Blockchain, or DLT in general, is in itself relatively unsuitable for storing large volumes of data, since updating in blocks increases the volume of data considerably. Rather, a mixed database/blockchain solution has to be pursued for large amounts of data. Here, larger amounts of data are saved and stored in the database. The associated blockchain, on the other hand, validates the stored status of the data and thus guarantees the authenticity and integrity of the data content. For example, a dataset is saved in the database. A checksum is generated and saved for the dataset. The checksum itself is also logged in the blockchain in order to record the data integrity in an unchangeable manner. This allows the data saved in the database to be verified.

FIG. 1 shows an exemplary method 100 for storing use data of a product. Here, in a first step 110, the use is first detected. This can be done by the product or a component thereof, or by an external device that detects the use, e.g. by the product being within detection range of the device, e.g. via WLAN, Bluetooth, or another radio technology, or by the product transmitting a corresponding signal to the device. The detection can be done optically, e.g. by reading a barcode, in 2D or 3D on the product, or electronically, e.g. by NFC (Near Field Communication).

Subsequently, in step 120, based on the detection of the use data, data concerning the detected use of the product is created. As described above, data can be detected here, such as the time of use, only as a day or also with additional information, such as time, location, time zone, etc. The use data may also contain an identification of the person or device using the product, which can be detected, for example, via an identification before use, further data of the use, i.e. type of use, duration of use, quantity and number of uses, number of switch-on and switch-off operations, or actions performed during use. The previously described identifications may also be performed in the case of desired anonymity via encrypted ID data, e.g., numbers, symbols, and the like, which are known only to a limited extent, e.g., only to the manufacturer, the owner, or only to public authorities. Step 120 may be performed by the product or a component thereof, or by an external device that has detected the use, or to which the detection has been communicated.

In a next step 130, the use data is then stored in a dataset in a retroactively non-modifiable form. The retroactively non-modifiable form here is, for example, as described above, a DLT such as blockchain. If applicable, the dataset is written to the blockchain in addition to already existing data blocks. The writing 130 may also be performed by the product or a component thereof, or by an external device that created the use data, or to which the use data was communicated. The writing may be performed on a memory located in the product, or in a memory associated with an external device.

Figure 2:
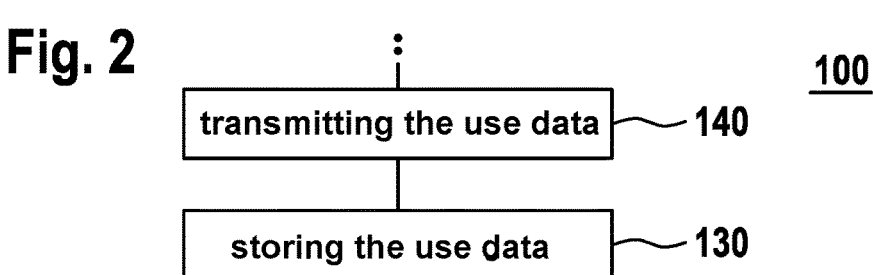

FIG. 2 shows that after creating 120 and before storing 130, the method 100 may comprise previously described transmitting 140 the use data to one or more computers each having a memory. In this case, the storing in step 130 may then be performed by one or more computers. Again, the writing may be performed on a memory located in the product or in a memory associated with an external device.

Figure 3:
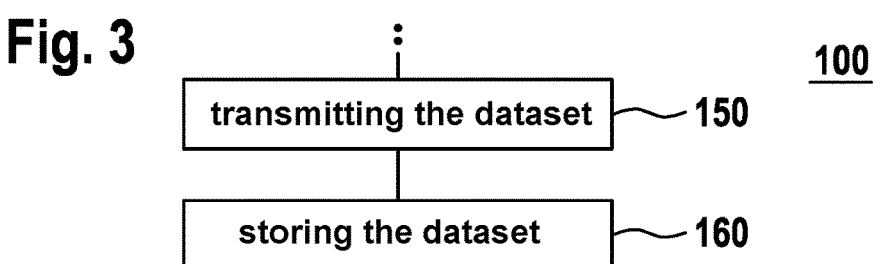

FIG. 3 shows that the method 100 may be executed in such a way that the storing in step 130 is first performed by the product in its own memory and then a previously described method is followed by transmitting 150 of the dataset to one or more computers, each of which has a memory, and then the dataset is stored by one or more computers in its/their memory. Since the dataset here already has the retroactively non-modifiable form from step 130, i.e. is present as a DLT or blockchain, this corresponds, for example, to the sidechain described above. This could then be inserted into a data construct already existing on the receiving computer, i.e., for example, the main blockchain, after transmitting 150. Alternatively, however, the computer may just have a simple database in which the sidechain is stored for further use at a later time.

Figure 4:
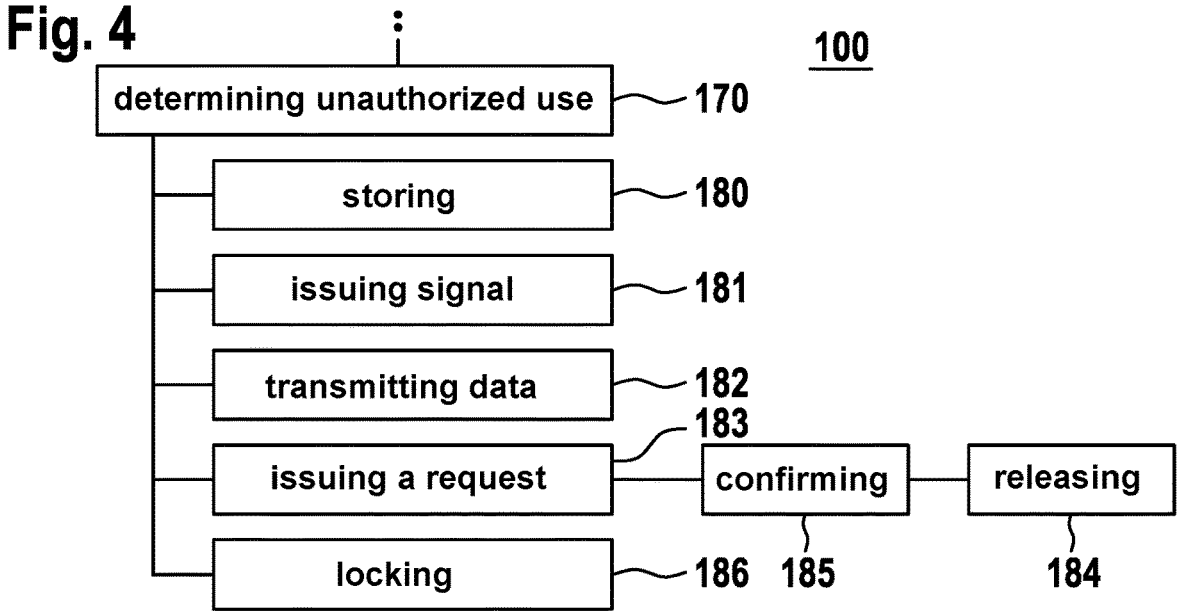

FIG. 4 shows that the method 100 as previously described may be followed, in response to a request for further use of the product, by a step 170 of determining that the further use represents an unauthorized use. This determination may be made, for example, by evaluating the data stored in the dataset and/or the data construct, as previously described. This step may also be performed in the product or in one of the previously described devices, or computers, respectively.

In the event that an unauthorized use has been determined in step 170, one or more of the following steps may follow in the method. In a step 180, the further use, or the request for a further use, may be stored in the dataset and/or the data construct. In a step 181, an optical and/or acoustic signal may be output. As previously described, this may occur at the product or at a location remote from the product. In a step 182, data may be transmitted, for example to a computer, such as one of those previously described, wherein the data there then causes a signal to be sent or a notification to be triggered at an external device. In a step 183, a request may be issued to a user, which the user has to confirm first. Whereby the receipt of the release in turn happens in step 185, and only afterwards in step 184 the release of the product is effected. As described previously, the request and release may be performed by the product itself or by another device described previously, such as a computer. Finally, in step 186, the product may be locked so that further use is not possible.

The steps described in connection with FIGS. 1 to 4 that involve transmitting data may use, for example, one or more of the following technologies: for example, Bluetooth, IR, LAN, WLAN, IoT, mobile radio, e.g., 2G, 3G, 4G, 5G, GSM, and/or LTE, LoRaWAN, and either directly or via intermediate stations, such as smart hubs, repeaters, routers, switches, mobile hotspots, data gates, access points, and/or the internet.

In the datasets and data constructs described in connection with FIGS. 1 to 4, each of which may be configured as a DLT or blockchain, one or more pieces of information may additionally be stored, from: information regarding article, serial number of the product and/or permitted use, such as an expiration date after which the product must no longer be used, or a permitted number of uses, wherein the information is written to the data construct during the manufacture of the product or is detected during the detection in step 110 of the use and is then stored in the dataset, or information regarding dates of manufacture, warehousing, shipment, sale of the product.

A system for processing data comprising a processor capable of executing the method as previously described is not shown. A computer program product and/or computer-readable storage medium, each comprising instructions that, when executed, implement the method as previously described, is also not described.

Figure 5:
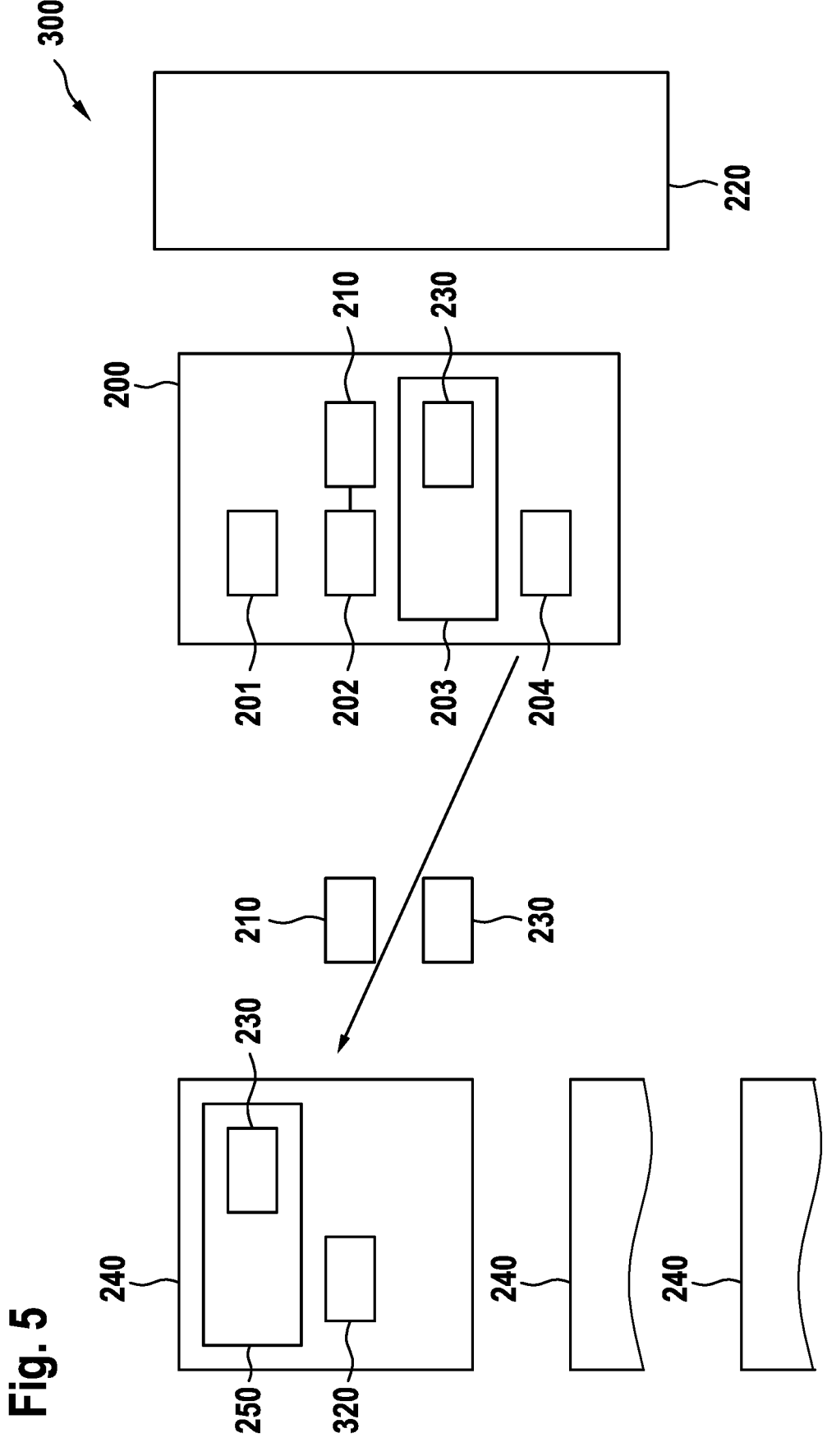
FIGS. 5 to 8 show schematic views of devices and systems of preferred embodiments.

FIG. 5 shows an exemplary device 200 for storing use data 210 of a product 220. The device comprises a detection unit 201, which detects the use of the product 220 in the manner described above.

Figure 6:
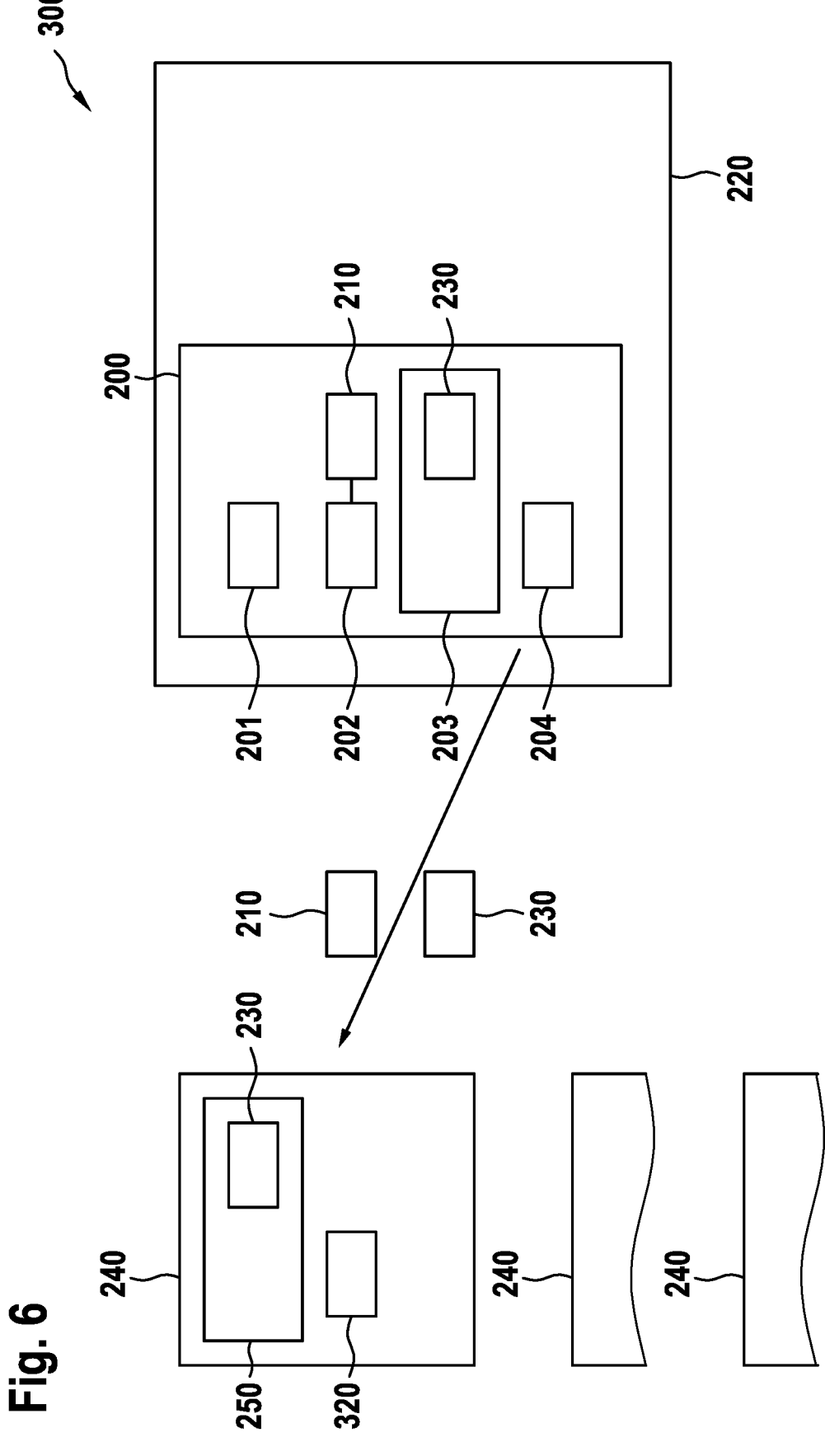

While in FIG. 5 the device 200 is a device independent of the product 220, FIG. 6 shows a configuration example in which the device 200 is a part of the product 220. However, the further relationships described previously and below are generally equally applicable to the embodiments of FIGS. 5 and 6.

If the device 200 represents a part of the product, the device 200 detects the use, for example, by direct signal transmission within the product 220.

If the device 200 is not part of the product, the use can be implemented, for example, by detecting that the product is within detection range of the device, e.g. via WLAN, Bluetooth, or another wireless technology, or by the product transmitting a corresponding signal to the device. The detection may also be done optically, e.g. by reading a barcode, in 2D or 3D on the product, or electronically, e.g. by NFC (Near Field Communication).

Furthermore, the device 200 comprises a data processing unit 202 that creates the use data 210 relating to the detected use of the product 220. The creation may be performed in the product or in an external device. As previously described, data may be detected here, such as the time of the use, only as a day or also with additional information, such as time, location, time zone, etc. The use data may further include an identification of the person or device using the product, which may be detected, for example, via an identification before use, further data of the use, i.e. type of use, duration of use, quantity and number of uses, number of switch-on and switch-off operations or actions performed during use. The previously described identifications may also be made in case of desired anonymity via encrypted ID data, e.g. numbers, symbols, and the like, which are only known to a limited extent, e.g. only to the manufacturer, the owner, or only to public authorities.

The device 200 further comprises a storage unit 203 that stores the use data 210 in a dataset 230 in a retroactively non-modifiable form. The retroactively non-modifiable form here is, for example, a blockchain, as described above. If applicable, the dataset is written to the blockchain in addition to existing data blocks. The storage unit may be part of the product or part of an external device that created the use data or to which the use data was communicated. The storage may be performed on a memory located in the product or in a memory associated with an external device.

It can further be seen that the device 200 may be part of a system 300, wherein the system 300 further comprises one or more computers 240, each having a memory 250. The device 200 then comprises a transmission unit 204 that transmits the use data 210 to one or more of the computers 240. The receiving computers then store in the respective memories 250, as previously described, the use data 210 in a dataset 230 in a retroactively non-modifiable form, namely a DLT or blockchain.

In such a system 300, the device 200 may again be implemented as part of the product 220, or externally, as shown in FIG. 5 or FIG. 6, respectively. The transmission unit 204 may also transmit the dataset 230 created in the device 200 to the one or more computers 240.

In other words, if the device 200 creates the dataset 230 from the use data 210, then that dataset 230 may be transmitted from the transmission unit 204 to the computer or computers 240 to be stored there or elsewhere. However, if the computer or computers 240 create the dataset 230 from the use data 210, then the use data 210 will be transmitted from the transmission unit 204 to the computer or computers 240 to be stored there or elsewhere in a dataset 230.

If the completed dataset 230 is transmitted to the computer or computers 240, the computer or computers 240 may include a calculation unit 241 that inserts the transmitted dataset 230 into an existing data construct 280 that is also not retroactively modifiable, i.e., that is also, for example, in DLT or as a blockchain.

Figure 7:
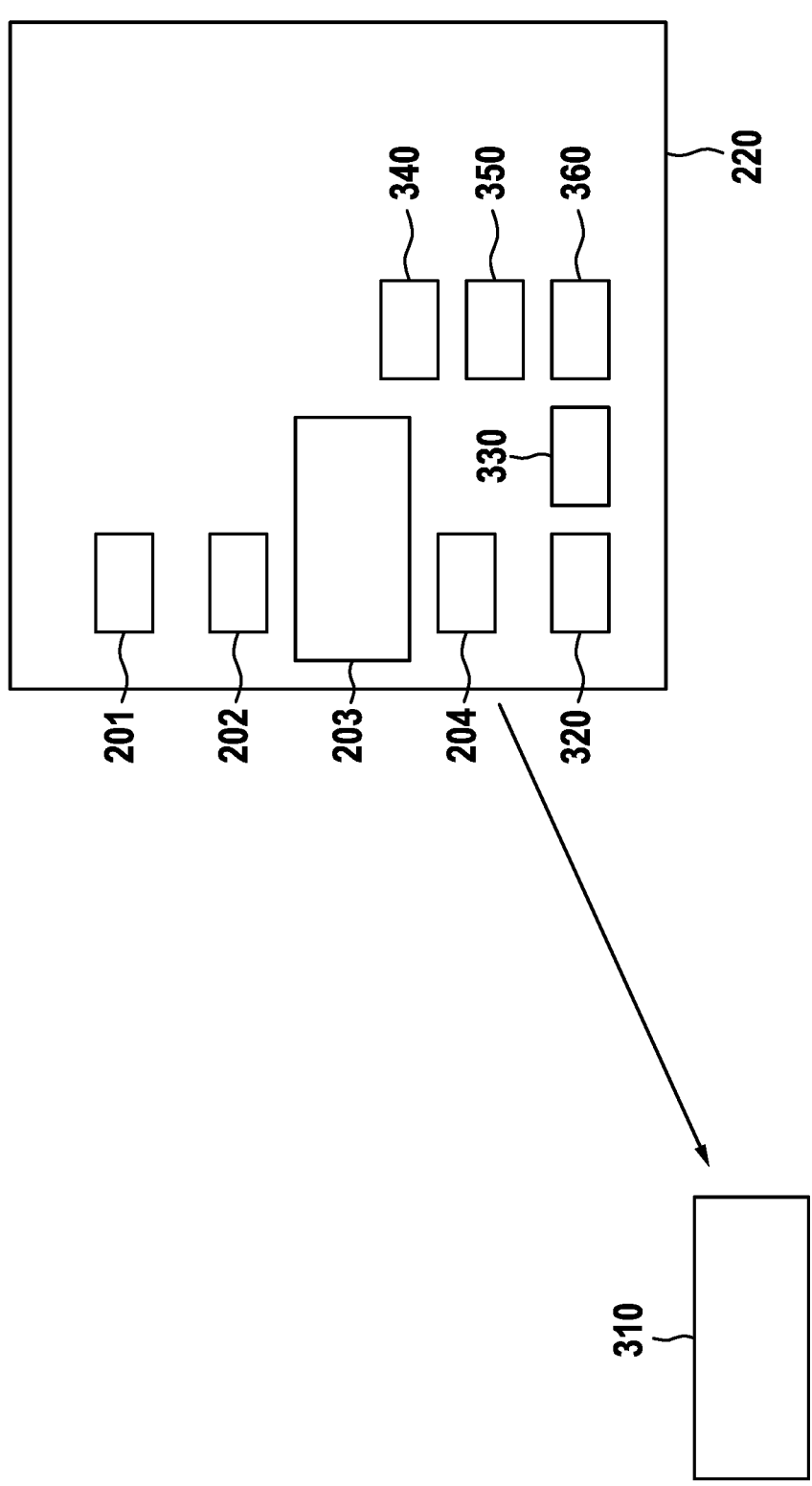

One of the computers 240 or, as shown in FIG. 7, the device 200 may include a determination unit 320 that, in response to a request for a further use, may determine that the further use constitutes an unauthorized use. This determination may be made, for example, by evaluating data stored in the dataset 230 and/or the data construct 280, as previously described.

Figure 8:
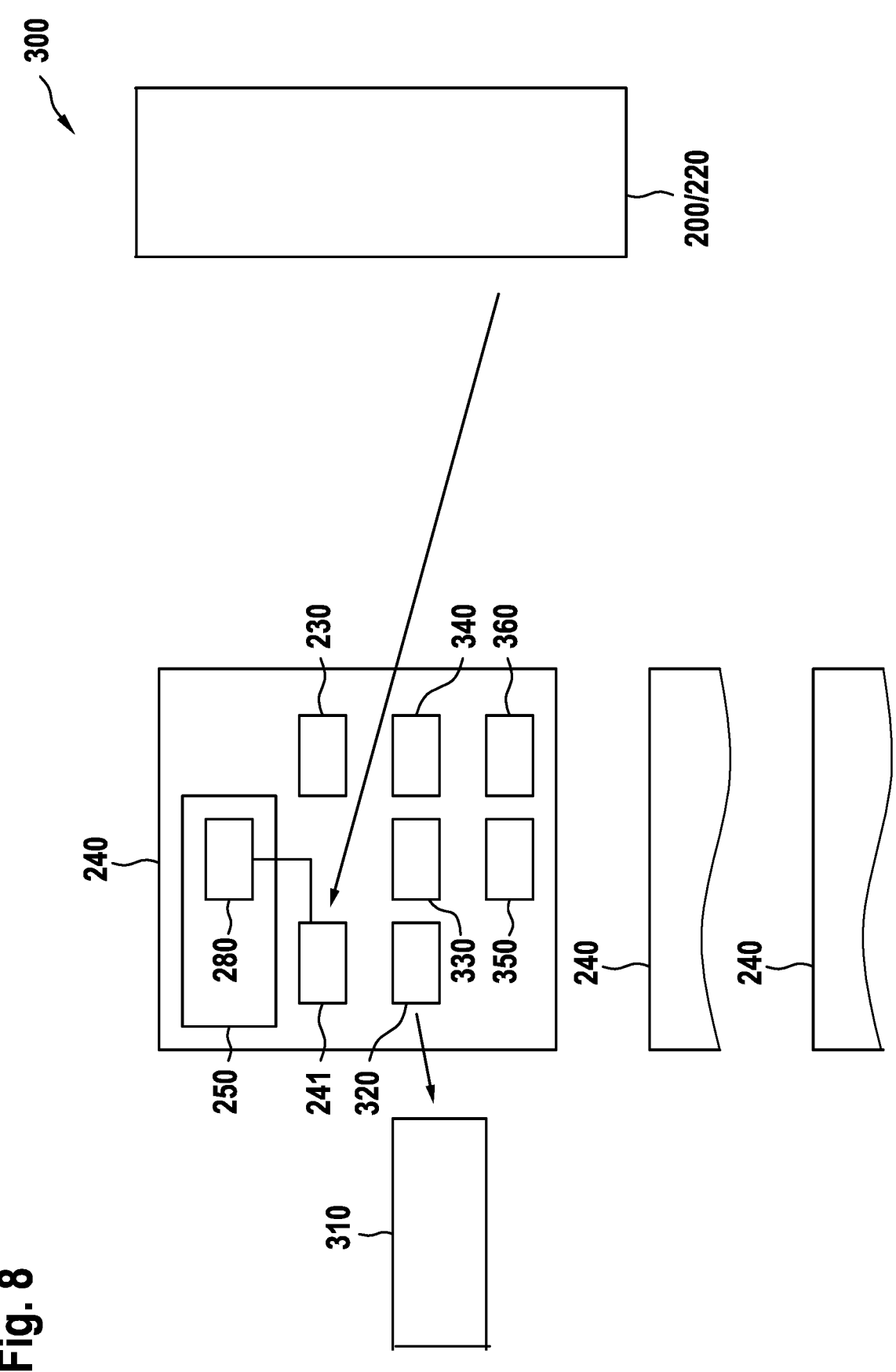

In the event that the determination unit 320 determines an unauthorized use, one or more of the computers 240, as shown in FIGS. 5, 6, and 8, or the device 200, as shown in FIG. 7, may include one or more of the following elements, or may be adapted in the following manner. The device 200 or the system 300 may store the further use in the dataset 230 and/or the data construct 280 if an unauthorized use is determined by the determination unit 320. A signaling device 330 may output an optical and/or acoustic signal if an unauthorized use has been determined by the determination unit 320. As previously described, this may occur at the product or at a location remote from the product. The transmission unit 204 may transmit data that causes a signal or notification to be issued at an external device 310 if an unauthorized use is determined by the determination unit 320. An output device 340 may output a request, and a release device 350, in response to receiving a user confirmation in response to the request, may release the product for the requested further use if an unauthorized use has been determined by the determination unit 320. A locking device 360 may lock the product 220 so that further use is not possible if an unauthorized use has been determined by the determination unit 320.

The elements described in connection with FIGS. 5 to 8 that involve transmitting data may use one or more of the following technologies, for example: Bluetooth, IR, LAN, WLAN, IoT, mobile radio, e.g., 2G, 3G, 4G, 5G, GSM, and/or LTE, LoRaWAN, and either directly or via intermediate stations, such as smart hubs, repeaters, routers, switches, mobile hotspots, data gates, access points, and/or the internet.

In the datasets 230 and data constructs 280 described in connection with FIGS. 5 to 8, each of which may be implemented as a DLT or blockchain, one or more pieces of information may additionally be stored, from: information regarding article, serial number of the product and/or a permitted use, such as an expiration date after which the product must no longer be used, or a permitted number of uses, wherein the information is written to the dataset when the product is manufactured or is detected when the use is detected and then stored in the dataset, or information regarding dates of manufacture, warehousing, shipment, sale of the product.

An exemplary embodiment of the device of FIG. 5 comprises a surgical motor system comprising a handpiece and a control device
   and a tool that is coupleable/connectable to the handpiece.

The tool forms the product 220. For example, the tool may be formed as a surgical milling cutter that is provided for machining bones. The tool is provided with a QR code as an ID element, which comprises at least an article number and a serial number. Alternatively, the tool may also have an RFID tag, an NFC tag or barcodes as ID element. The ID element contains at least one serial number, which can be read electronically in an embodiment as an RFID or NFC tag and optically in an embodiment as a QR code or bar code.

The handpiece comprises the detection unit 201. In this configuration example, the detection unit is configured as an optical reader unit that is provided to read the QR code on the tool. Alternatively, the detection unit may also be configured as an RFID reader or an NFC reader. The detection unit 201 is arranged in the handpiece. If the tool is inserted into the handpiece or connected to the handpiece, the detection unit 201 detects the ID element and determines at least the serial number.

The control device comprises the data processing unit 202, the storage unit 203 and the transmission unit 204. The handpiece is connected to the control device in a ready-to-use state. When the tool is coupled to the handpiece, the detection unit 201 reads the ID element. The data processing unit 202 generates use data 210 via the serial number determined from the ID element and, if applicable, other data detected during an operation. The use data is then stored as a retroactively non-modifiable dataset in the storage unit 203.

The transmission unit 204 is provided to connect the control device to the computer 240. The computer 240 is preferably configured as a local server, for example, an intranet server for a hospital. In order to connect the control device to the local server, the system 300 comprises access points not shown in detail. The transmission unit 204 is provided for wireless connection to the access points. The computer 240 and the access points may be wired, for example via a LAN connection, or may be wirelessly connected to the computer 240.

The server comprises the determination unit 320. The determination of whether a use of the product 200 is permitted or not is made centrally on the server 200. If the determination unit 320 detects an unauthorized use, the computer 240 sends corresponding information to the device 200. In the embodiment as a control device, the device 200 comprises a display on which the information can be shown. Various functions may be stored in the device for processing the information about an unauthorized use. For example, if the determination unit 320 detects that the tool is a single-use tool that has already been used, the control device presents the corresponding information. It is also conceivable that the control device may lock the use of the tool, wherein functions may be provided to allow emergency operation.

An exemplary embodiment of the device 200 of FIG. 6 is a medical pump, for example an infusion pump. The use data 210, which is stored in the dataset 230 in a retroactively non-modifiable form, may be, for example, information on performed service checks. Additionally, each time the device 200 is used, a dataset 230 is created that contains use data 210 about the startup. If the determination unit 320 detects that the dataset 230 with use data 210 about the startup belongs to a device for which the last dataset 230 with use data 210 about a performed service check has expired, the device 220 configured as a medical pump can output a signal that the service check has expired.

For example, an exemplary embodiment for FIG. 8 is an embodiment of the product 220 as an infusion bag, for example. In such an embodiment, the device 200 may be configured as a holder for the infusion bag. Alternatively, however, it is also conceivable to configure the device 200 as a hand-held scanner or the like, as is used, for example, for incoming or outgoing goods in a warehouse. The device 200 is provided to detect at least one identification number of the product 220, such as a batch number. Depending on the configuration of the device 200, different methods can be used. In the handheld scanner embodiment, the device may be provided for optical recognition of a barcode or a QR code. In the embodiment as a holder, the device may be provided for reading an NFC or RFID tag.

For such products, in particular, manufacturing, warehousing, and transportation are monitored. If it is subsequently determined that a circumstance has occurred in the process that requires the product 220 to be locked, a dataset 230 containing this information for the product is stored in the data construct 280. The device 220 is connected to the computer 240. If the device 220 is a handheld scanner, the computer 240 may be, for example, a computer of a warehouse management system. For example, if the device 220 is a holder, the computer 240 may be part of a patient monitoring system. In particular, in such an embodiment, device 310, which is separate from the computer 240, is advantageous in order to ensure that the user is informed that the product 220 is locked. For example, the device 310 may be configured as an LED by which the locking is signaled.

An alternative tracking system according to a further preferred embodiment may be configured as follows (not shown). The medical tracking system serves to securely track and document the history of a disposable medical product configured in the form of a scalpel. A QR code with an encoded, bijective serial number is engraved in an outer surface of the scalpel, which can be detected and read by a reading device in the form of a camera. In a computer network with a plurality of computers (in this case more than twenty computers), a respective digital tracking book with a directory of information blocks relating to the at least one disposable medical product is stored decentrally as a blockchain in the computers, wherein the serial number, the article number and a control number of the medical product are stored in a first block and this data is self-contained via a first hash or hash value. The first hash is used to check the stored data and closes the dataset/block, so to speak. If the data of the first block were subsequently changed, the first hash would necessarily change as well. If the scalpel is now read in via the reading device prior to a use in an operating room, a use transaction is sent to the computer network when a first use is detected and a use block with a time stamp, the use transaction and a use hash (for re-completion of the block) is created via a block generation module which is adapted to create this use block on the basis of the use transaction and the first hash and to make it available to the computer network in order to add this use block to the respective blockchain in the computers of the computer network. If, contrary to the specification, the disposable medical product is used again, it would first have to be read in again with the help of the reading device. A tracking module is adapted to read out the blockchain for at least one disposable medical product and to detect an existing application block (with corresponding application transaction) in the blockchain. Instead of now adding a second application block, the tracking module is configured to output a visual alarm via an OP monitor and to additionally generate an acoustic signal. In this way, repeated use can be safely avoided and the user can be informed about the unauthorized two-way use.

In particular, the following aspects are disclosed in accordance with the present invention:

1. aspect computer-implemented method (100) for storing use data (210) of a product (220), wherein the method (100) comprises:

detecting (110) a use of the product (220);

creating (120) use data (210) pertaining to the detected use of the product (220); and storing (130) the use data (210) in a dataset (230) in a retroactively non-modifiable form, wherein the dataset (230) uses blockchain technology.

2. aspect method (100) according to aspect 1, wherein the method (100) further comprises, after creating(120) and before storing (130):

transmitting (140) the use data (210) to at least one computer (240), each comprising a memory (250); and wherein storing (130) is performed by the at least one computer (240) in the respective memory (250).

3. aspect method (100) according to aspect 1 or 2, wherein storing (130) is performed by the product (220) in a dedicated memory (245) wherein the method (100) further comprises:

transmitting (150) the dataset (230) to at least one computer (240), each comprising a memory (250); and storing (160) the dataset (230) from the at least one computer (240) in the respective memory (250).

4. aspect method (100) according to aspect 3, wherein after the dataset (230) of the product (220) is transmitted (150) in the at least one computer (240), the dataset (230) is inserted into an existing data construct (280) that is also not retroactively modifiable.

5. aspect method (100) according to aspect 4, wherein the data construct (280) uses blockchain technology.

6. aspect method (100) according to one of aspects 1 to 5, wherein the blockchain technology is configured in one of the following forms:

blockchain stored only in memories (250) of non-public computers (240) of a group (260);

blockchain stored in memories (250) of non-public computers (240) of at least two groups (260, 270); or blockchain stored in memories (250) of public computers (240).

7. aspect method (100) according to one of aspects 2 to 6, wherein one or more of the steps of transmitting (140) the use data and transmitting (150) the dataset (230) uses one or more of the following technologies, for example: Bluetooth, IR, LAN, WLAN, IoT, mobile radio, e.g., 2G, 3G, 4G, 5G, GSM, and/or LTE, LoRaWAN, and transmitted either directly or via intermediate stations, such as smart hubs, repeaters, routers, switches, mobile hotspots, data gates, access points, and/or the internet.

8. aspect method (100) according to one of aspects 1 to 7, wherein in the dataset (230) and/or the data construct (280) additionally one piece or more pieces of information is/are stored, including:

information regarding article, serial number of the product and/or a permitted use, such as an expiration date after which the product must no longer be used, or a permitted number of uses, wherein the information is written into the data construct (280) when the product (220) is manufactured or is detected when the use is detected (110) and then stored in the dataset (230);

information regarding dates of manufacture, warehousing, shipment, sale of the product (220).

9. aspect method (100) according to one of aspects 1 to 8, wherein the product (220) is a medical product.

10. aspect method (100) according to one of aspects 1 to 9, further comprising:

in response to a request for a further use of the product (220): determining (170), in the product (220) or a computer (240), that the further use constitutes an unauthorized use by evaluating the data stored in the dataset (230) and/or the data construct (280).

11. aspect method (100) according to aspect 10, furthermore comprising:

if an unauthorized use was determined in step (170), performing one or more of the following steps:

storing (180) the further use in the dataset (230) and/or the data construct (280);

issuing (181) an optical and/or acoustic signal;

transmitting (182) data causing a signal or triggering a notification at an external device (310);

issuing (183) a request, and releasing (184) the requested further use only after receiving (185) a user confirmation;

locking (186) the product (220) so that further use is not possible.

12. aspect system for processing data, comprising a processor adapted to perform the method according to any one of aspects 1 to 11.

13. aspect computer program product comprising instructions that, when the program is executed by a computer, cause the computer to execute the method according to one of aspects 1 to 11.

14. aspect computer-readable storage medium comprising instructions that, when executed by a computer, cause the computer to execute the method according to one of aspects 1 to 11.

15. aspect device (200) for storing use data (210) of a product (220), characterized by:

a detection unit (201) configured to detect a use of the product (220);

a data processing unit (202) configured to create the use data (210) relating to the detected use of the product (220); and a storage unit (203) configured to store the use data (210) in a dataset (230) in a retroactively non-modifiable form, wherein the dataset (230) uses blockchain technology.

16. aspect system (300) comprising a device (200) according to aspect 15, and at least one computer (240), each comprising a memory (250), wherein the device (200) further comprises:

a transmission unit (204) adapted to transmit the use data (210) to the at least one computer (240); and wherein the respective memories (250) are adapted to store the use data (210) in a dataset (230) in a retroactively non-modifiable form.

17. aspect system (300) comprising a device (200) according to aspect 15, and at least one computer (240), each comprising a memory (250), wherein the device (200) is implemented as part of the product (220), and furthermore comprises:

a transmission unit (204) configured to transmit the dataset (230) to the at least one computer (240); and wherein the respective memories (250) are configured to store the dataset (230), wherein the data construct (280) uses blockchain technology.

18. aspect system (300) according to aspect 17, wherein the at least one computer (240) furthermore comprises a calculation unit (241) configured to insert the dataset (230) transmitted from the device (200) into an existing data construct (280) that is also not retroactively modifiable.

19. aspect device (200) or system (300) according to one of aspects 15 to 18, wherein the DLT is implemented in one of the following forms:

blockchain stored only in memories (250) of non-public computers (240) of a group;

blockchain stored in memories (250) of non-public computers (240) of at least two groups; or blockchain stored in memories (250) of public computers (240).

20. aspect system (300) according to one of aspects 17 to 19, wherein the transmission unit (204) uses one or more of the following technologies: Bluetooth, IR, LAN, WLAN, IoT, mobile radio, e.g., 2G, 3G, 4G, 5G, GSM, and/or LTE, LoRaWAN, and transmits data either directly or via intermediate stations, such as smart hubs, repeaters, routers, switches, mobile hotspots, data gates, access points, and/or the internet.

21. aspect device (200) or system (300) according to one of aspects 15 to 20, furthermore configured to store in the dataset (230) and/or the data construct (280) additionally one piece or more pieces of information comprising:

information regarding article, serial number of the product and/or a permitted use, such as an expiration date after which the product must no longer be used, or a permitted number of uses, wherein the information is written into the data construct (280) during the manufacturing of the product (220) or is detected during the detection of the use and then stored in the dataset (230);

information regarding dates of manufacture, warehousing, shipment, sale of the product (220).

22. aspect device (200) or system (300) according to one of aspects 15 to 21, further comprising:

a determination unit (320) configured to determine, in response to a request for further use of the product (220), that the further use is an unauthorized use by evaluating the data stored in the dataset (230) and/or the data construct (280).

23. aspect device (200) or system (300) according to aspect 22, wherein the device (200) or system (300) is furthermore configured to store the further use in the dataset (230) and/or the data construct (280) if an unauthorized use has been determined by the determination unit (320);

wherein the device (200) or system (300) furthermore comprises a signaling device (330) configured to output a visual and/or audible signal if an unauthorized use has been determined by the determination unit (320);

wherein the transmission unit (204) is furthermore configured to transmit data causing a signal or triggering a notification at an external device (310) if an unauthorized use has been determined by the determination unit (320);

wherein the device (200) or system (300) furthermore comprises an output device (340) configured to output a request, and release device (350) configured, in response to receiving a user confirmation in response to the request, to release the product for the requested further use if an unauthorized use has been determined by the determination unit (320); and/or wherein the device (200) or system (300) further comprises a locking device (360) configured to lock the product (220) from further use if an unauthorized use has been determined by the determination unit (320).

The invention claimed is:

1. A computer-implemented medical tracking method for secure tracking and storage of application data of a medical product, the computer-implemented medical tracking method comprising the steps of:

detecting an application of the medical product;

creating application data pertaining to the application of the medical product;

storing the application data in a dataset in a retroactively non-modifiable form, wherein the dataset uses blockchain technology;

detecting a bijective identification of the medical product;

calculating, based on the bijective identification, a first hash value;

storing a first block with the bijective identification and the first hash value in a blockchain on each computer of a computer network comprising at least three computers;

detecting the application of the medical product by a detection unit and sending an application transaction to the computer network;

checking, by a tracking module, whether an application block exists in the blockchain for the medical product;

generating, when no application block exists, an application block with the first hash value, a time stamp, the application transaction, and an application hash by a block generation module based on the application transaction, and providing the application block to the computer network to add the application block to the blockchain in the at least three computers of the computer network, respectively; and issuing, when an application block exists, an alarm and/or blocking a functionality of the medical product.

2. The computer-implemented medical tracking method according to claim 1, further comprising the steps of:

storing, in the first block, a minimum durability date of the medical product; and in addition to the step of detecting the application, comparing the time stamp to the minimum durability date, and upon exceeding the minimum durability date: issuing an alarm and/or locking a functionality of the medical product.

3. The computer-implemented medical tracking method according to claim 1, wherein the computer-implemented medical tracking method performs locking of the functionality of the medical product by interrupting a power supply to the medical product.

4. The computer-implemented medical tracking method according to claim 1, further comprising the steps of:

after issuing the alarm and/or locking the functionality of the medical product, requesting a user to perform a confirmation input via an input device and to confirm that the medical product is to be used again;

detecting the confirmation input by the user; and generating an alarm block with a time stamp, an alarm transaction, and an alarm hash, and providing the alarm block to the computer network in order to add the alarm block to the respective blockchain in the at least three computers of the computer network and documenting a repeated application.

5. The computer-implemented medical tracking method according to claim 1, further comprising the steps of:

in addition to the bijective identification with a bijective serial number: storing a unique control number associated with the bijective serial number in the first block generated by a predetermined non-public algorithm as an alphanumeric code; and upon detection of the application of the medical product:
verifying the bijective serial number and the unique
control number associated with the bijective serial
number and determining that the medical product is
counterfeit if the unique control number does not match
the bijective serial number.

6. The computer-implemented medical tracking method
according to claim 1, further comprising the steps of:
detecting a warehouse entry by detecting the unique
identification of the medical product by a warehouse-
entry detection device;
generating a warehouse block having a warehouse trans-
action and a time stamp as a warehouse entry date and
a warehouse hash, and providing to the computer
network to add said warehouse block to the respective
blockchain in the at least three computers of the com-
puter network to document a warehouse entry.

7. A non-transitory computer-readable storage medium
comprising instructions that, when executed by a computer,
cause the computer to execute the computer-implemented
medical tracking method according to claim 1.

8. A medical tracking system for secure tracking of a
disposable medical product, the medical tracking system
comprising:
a disposable medical product to be tracked, which has a
bijective identification;
at least one detection unit adapted to detect the bijective
identification of the disposable medical product and to
provide the bijective identification in a computer-read-
able form; and
a computer network with at least three computers, on each
of which a digital tracking book with a directory of
information blocks relating to the disposable medical
product is stored in a decentralized manner as a block-
chain;
an application module adapted to send an application
transaction for the disposable medical product to the
computer network upon detection of the disposable
medical product by the detection unit for an applica-
tion;
a block generation module adapted to create, based on the
application transaction and the first hash, an application
block with a time stamp, the application transaction,
and an application hash, and to make the application
block available to the computer network in order to add
the application block to the blockchains in the com-
puters of the computer network; and
a tracking module adapted to read out the blockchain for
the disposable medical product and to detect an existing
application block in the blockchain and to issue an
alarm and/or lock an application of the disposable
medical product when an application is detected again.

9. The medical tracking system according to claim 8,
wherein the bijective identification is engraved in the dis-
posable medical product and the detection unit has an optical
detection unit and/or the bijective identification is stored in
an RFID tag of the disposable medical product and the
detection unit has an RFID reader.

10. The medical tracking system according to claim 8,
wherein the disposable medical product is a medical instru-
ment and/or a sieve basket and/or a medical holder and/or an
electrically operated medical device.

11. The medical tracking system according to claim 8,
wherein, in addition to the bijective identification, a mini-
mum durability date for the disposable medical product is
stored in the first block, and the tracking module is adapted
to compare the time stamp with the minimum durability date in response to an application of the disposable medical
product and to issue an alarm and/or lock an application of
the disposable medical product when the minimum durabil-
ity date is exceeded.

12. The medical tracking system according to claim 10,
wherein the disposable medical product is an electrically
operated medical device, and the tracking module is adapted
to interrupt an electrical power supply to the disposable
medical product upon a repeated application or upon
exceeding a minimum durability date of the disposable
medical product to lock an application.

13. The medical tracking system according to claim 8,
further comprising a central database with at least one
database entry stored for the disposable medical product,
wherein an entry hash is generated for the at least one
database entry, and the entry hash is stored in the blockchain
to secure the at least one database entry against manipulation
via the entry hash.

14. A device for tracking and storing application data of
a medical product, the device comprising:
a detection unit configured to detect an application of the
medical product, the detection unit configured to detect
a bijective identification of the medical product;
a data processing unit configured to create the application
data relating to the application of the medical product,
the data processing unit configured to calculate a first
hash value based on the bijective identification of the
medical product; and
a storage unit configured to store the application data in a
dataset using blockchain technology in a retroactively
non-modifiable form, the storage unit configured to
store a first block with the bijective identification and
the first hash value in a blockchain on each computer of
a computer network comprising at least three comput-
ers;
an application module configured to detect an application
of the medical product by the detection unit and send an
application transaction to the computer network;
a tracking module configured to check whether an appli-
cation block exists in the blockchain for the medical
product; and
a block generation module configured to generate, when
no application block exists, an application block with
the first hash value, a time stamp, the application
transaction, and an application hash based on the appli-
cation transaction, and to provide the application block
to the computer network to add the application block to
the blockchain in the at least three computers of the
computer network, respectively,
the tracking module configured to issue an alarm and/or
block a functionality of the medical product when an
application block exists.

15. The medical tracking system according to claim 8,
wherein at least the bijective identification of the disposable
medical product and an associated first hash are stored in a
first block.

16. The medical tracking system according to claim 9,
wherein the bijective identification is a serial number and/or
a QR code.

17. The medical tracking system according to claim 13,
wherein the at least one database entry is a medical docu-
mentation of the disposable medical product.

18. The medical tracking system according to claim 8,
wherein the application module is further adapted to add a
dead-end marker to a corresponding medical product of the
blockchain in addition to the application transaction when a
minimum durability date is exceeded in order to reliably and quickly recognize that the corresponding medical product is no longer usable in the event of a repeated application.

*     *     *     *     *